(12) United States Patent
Gandhi et al.

(10) Patent No.: US 9,205,458 B2
(45) Date of Patent: Dec. 8, 2015

(54) METHOD AND APPARATUS FOR SORTING FIBERS

(71) Applicant: Toyota Motor Engineering & Manufacturing North America, Inc., Erlanger, KY (US)

(72) Inventors: Umesh N. Gandhi, Farmington Hills, MI (US); Raghuram Mandapati, Westland, MI (US)

(73) Assignee: Toyota Motor Engineering & Manufacturing North America, Inc., Erlanger, KY (US)

( * ) Notice: Subject to any disclaimer, the term of this patent is extended or adjusted under 35 U.S.C. 154(b) by 100 days.

(21) Appl. No.: 13/944,812

(22) Filed: Jul. 17, 2013

(65) Prior Publication Data
US 2015/0021238 A1    Jan. 22, 2015

(51) Int. Cl.
| | |
|---|---|
| *B07B 1/06* | (2006.01) |
| *B07B 1/42* | (2006.01) |
| *G01N 1/40* | (2006.01) |
| *G01N 5/04* | (2006.01) |
| *B07B 13/04* | (2006.01) |

(52) U.S. Cl.
CPC ... *B07B 1/06* (2013.01); *B07B 1/42* (2013.01); *G01N 1/4077* (2013.01); *G01N 5/04* (2013.01); *B07B 13/04* (2013.01); *B07B 2201/04* (2013.01); *B07B 2230/01* (2013.01); *B07B 2230/04* (2013.01); *G01N 2001/4094* (2013.01)

(58) Field of Classification Search
CPC ........ B07B 1/00; B07B 1/40; B07B 2230/04; B07B 2201/04
USPC ....................... 209/13, 17, 234, 268, 311, 315
See application file for complete search history.

(56) References Cited

U.S. PATENT DOCUMENTS

| | | | | |
|---|---|---|---|---|
| 3,305,481 | A * | 2/1967 | Peterson | 210/785 |
| 4,062,768 | A * | 12/1977 | Elliot | 209/341 |
| 4,212,848 | A * | 7/1980 | Boehme et al. | 422/267 |
| 5,672,399 | A | 9/1997 | Kahlbaugh et al. | |
| 5,799,643 | A * | 9/1998 | Miyata et al. | 125/21 |
| 6,267,310 | B1 * | 7/2001 | Cappola | 241/69 |
| 6,925,857 | B2 * | 8/2005 | Weber et al. | 73/64.54 |
| 7,763,410 | B2 * | 7/2010 | Yamaguchi et al. | 430/137.2 |
| 7,909,990 | B2 * | 3/2011 | Takahashi et al. | 210/86 |
| 8,915,377 | B2 * | 12/2014 | Gandhi | 209/539 |

(Continued)

FOREIGN PATENT DOCUMENTS

GB    2470075 A    11/2010

OTHER PUBLICATIONS

Roop Telsonic, "Sonoscreen, Ultrasonic Supported Sieving Technology," undated website advertisement, 2 pages, Mumbai, India.

*Primary Examiner* — Jeremy R Severson
(74) *Attorney, Agent, or Firm* — Christopher G. Darrow; Darrow Mustafa PC (57) ABSTRACT

An apparatus and methods for sorting and determining the length distribution of fibers in a sample are disclosed. One method of sorting and determining the length distribution of fibers includes immersing the fibers in a liquid to form a mixture; placing the mixture into a stack of sieves; progressively applying a predetermined number of frequencies of sound energy to each sieve in the stack of sieves; draining the mixture from the stack of sieves; and quantifying the collected fibers in each sieve in the stack of sieves.

15 Claims, 6 Drawing Sheets

(56) References Cited

U.S. PATENT DOCUMENTS

| | | | |
|---|---|---|---|
| 2006/0266284 A1* | 11/2006 | Fritz et al. | 118/308 |
| 2010/0165462 A1* | 7/2010 | Kawai et al. | 359/513 |
| 2012/0024764 A1* | 2/2012 | Krush et al. | 209/326 |
| 2013/0213862 A1* | 8/2013 | Peterson | 209/235 |
| 2014/0048456 A1* | 2/2014 | Adams et al. | 209/325 |
| 2014/0291216 A1* | 10/2014 | Brunone | 209/365.3 |

* cited by examiner

METHOD AND APPARATUS FOR SORTING FIBERS

BACKGROUND

A fiber reinforced polymer (FRP) is a composite material including a polymer matrix reinforced with fibers such as glass, carbon, or plastic to improve the strength, rigidity, and impact resistance of the polymer. The properties of an FRP depend on the fiber length, fiber distribution, and fiber orientation within the polymer matrix. In order to optimize one or more properties of the FRP, the length distribution of fibers present in various samples of the FRP can be measured.

To measure the distribution of fibers of different lengths in a FRP sample, the fibers can be separated from the polymer matrix using heat. The fibers can then be suspended in a liquid and sorted according to length using a stack of sieves having progressively smaller screens. The weight of fibers present in each screen after the sorting process can be determined in order to calculate the overall fiber length distribution for a given sample of the FRP. However, the fibers have a tendency to attract each other, with smaller fibers adhering to longer fibers within the layers of the sieve stack, skewing the fiber length distribution results.

SUMMARY

An improved apparatus and methods for sorting and determining the length distribution of fibers present in a given sample of an FRP are disclosed. The methods include forming a mixture of liquid and fibers and passing the mixture through a stack of sieves using a progressive application of tuned frequencies at each level of the stack. The improved apparatus includes a stack of sieves, a control device, one or more sonicating devices configured to apply a pattern of frequencies to the sieves, and a drain for removing the liquid from the stack of sieves.

One aspect of the disclosed embodiments is a method of sorting and determining the length distribution of fibers. The method includes immersing the fibers in a liquid to form a mixture; filling a stack of sieves with the mixture; progressively applying two or more frequencies of sound energy to each sieve in the stack of sieves; draining the mixture from the stack of sieves; and quantifying the collected fibers in each sieve in the stack of sieves.

Another aspect of the disclosed embodiments is an apparatus for sorting fibers. The apparatus includes a stack of sieves of progressively graduated filtering size for sorting the fibers in a mixture of fibers and liquid and a sonicating device configured to apply multiple frequencies of sound energy to each sieve in the stack of sieves. The apparatus further includes a control device configured to implement the multiple frequencies of sound energy in a pattern selected by an operator and a drain for removing the liquid from the stack of sieves.

Another aspect of the disclosed embodiments is a method of sorting and determining the length distribution of fibers. The method includes immersing the fibers in a liquid to form a mixture; placing the mixture into a stack of sieves; progressively applying a predetermined number of frequencies of sound energy to each sieve in the stack of sieves; draining the mixture from the stack of sieves; and quantifying the collected fibers in each sieve in the stack of sieves.

BRIEF DESCRIPTION OF THE DRAWINGS

The description herein makes reference to the accompanying drawings wherein like reference numerals refer to like parts throughout the several views, and wherein.

DETAILED DESCRIPTION

Both an improved apparatus and methods for sorting and determining the length distribution of fibers from an FRP sample are disclosed. One example apparatus includes a stack of sieves of progressively graduated filtering size for sorting the fibers from a mixture of fibers and liquid. The fibers are suspended in the liquid before sorting, and the liquid can be a polar liquid, a non-polar liquid, or a polar liquid treated with an additive to encourage the fibers to repel one another. The use of an additive or non-polar liquid is not adequate for accurate length distribution determination, so the apparatus can be improved by including a sonicating device configured to apply multiple frequencies of sound energy to each sieve in the stack of sieves and a control device configured to implement the multiple frequencies of sound energy in a pattern selected by an operator. Both the prior art system and the improved system are described in reference to the figures below.

Figure 1:
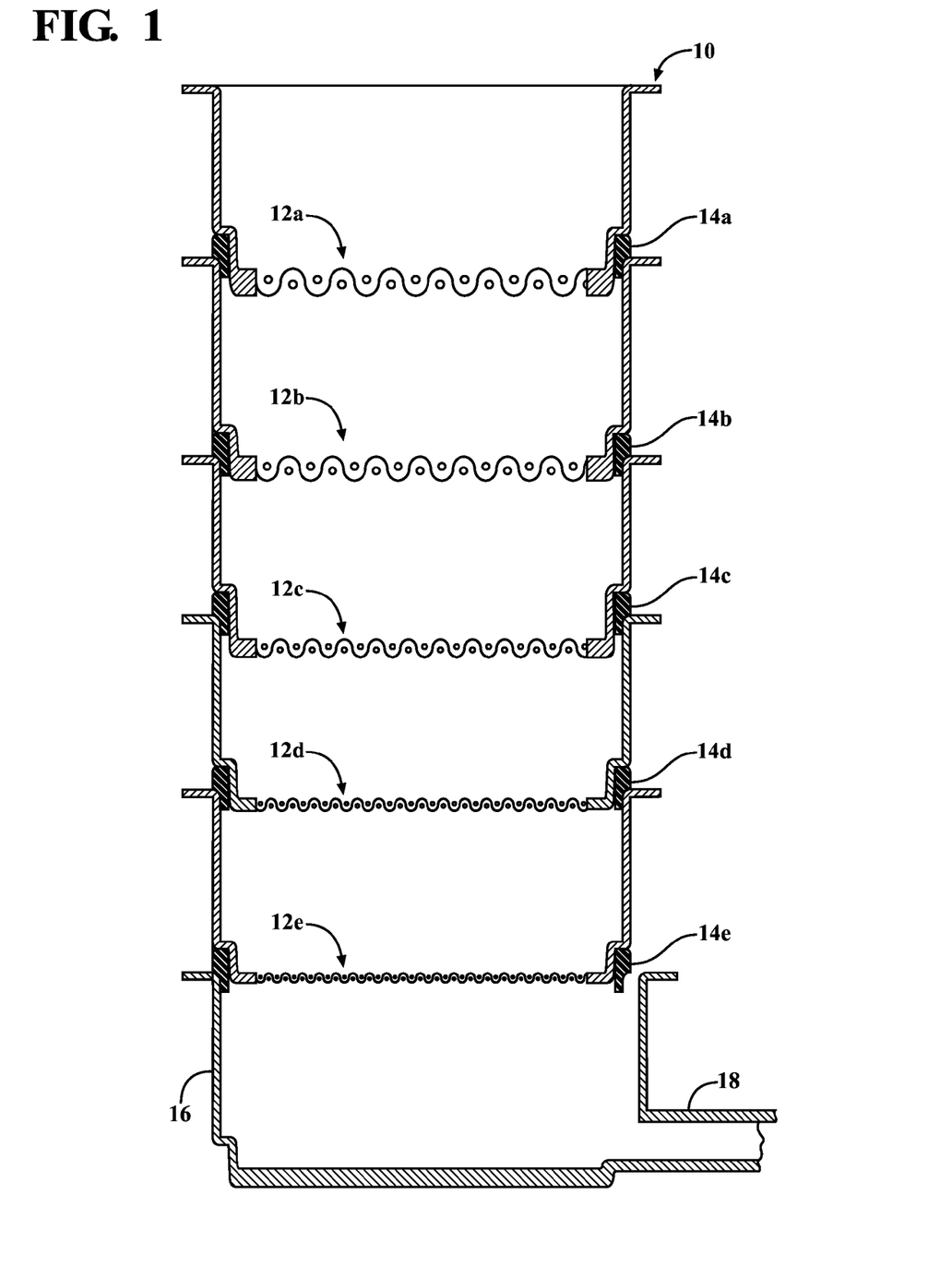
FIG. 1 is a sectional side view of a prior art sieve stack for sorting fibers.

FIG. 1 is a sectional side view of a prior art sieve stack 10 for sorting fibers from a sample. The sieve stack 10 in the example shown here includes five sieves 12a-e of woven construction, with the top sieve 12a having the largest openings sized to capture the longest fibers and the bottom sieve 12e having the smallest openings sized to capture the shortest fibers in the sample. Though five sieves 12a-e are shown in this example, the total number of sieves and the incremental size of the openings within each sieve are selected according to the known or expected distribution of lengths of fibers in the sample.

The top sieve 12a is configured to receive a mixture of liquid and fibers for sorting, and can be capped by a lid (not shown) after introduction of the mixture. The liquid can be water or another polar liquid, a non-polar liquid such as silicone oil, turpentine, benzene, carbon tetrachloride, diethyl ether, or any other organic solvent, or a solution of water and an additive. A non-polar liquid or additive can coat the fibers and help the fibers repel one another for sorting purposes. In the example shown, 5 ring-style seals 14a-e are situated between corresponding sieves 12a-e in order to avoid leaks between each of the layers of the sieve stack 10.

A collection unit 16 and drain 18 are located at the bottom of the sieve stack 10 below the bottom sieve 12e. The collection unit 16 receives excess liquid and any remaining particulates from the mixture after the fibers have been captured by each of the sieves 12a-e. The drain 18 can be opened to remove the excess liquid after the sorting process. Once the excess liquid is removed, the sieves 12a-e can be removed from the sieve stack 10, dried, and the collected fibers in each sieve 12a-e can be quantified, for example, by comparing the weight of the dried sieves 12a-e before and after the mixture has passed through the sieve stack 10. However, the sieve stack 10 of FIG. 1 fails to adequately separate and sort the fibers so that an accurate length distribution can be calculated. An example of one of the problems that occurs when using the prior art sieve stack 10 is shown in FIG. 2.

Figure 2:
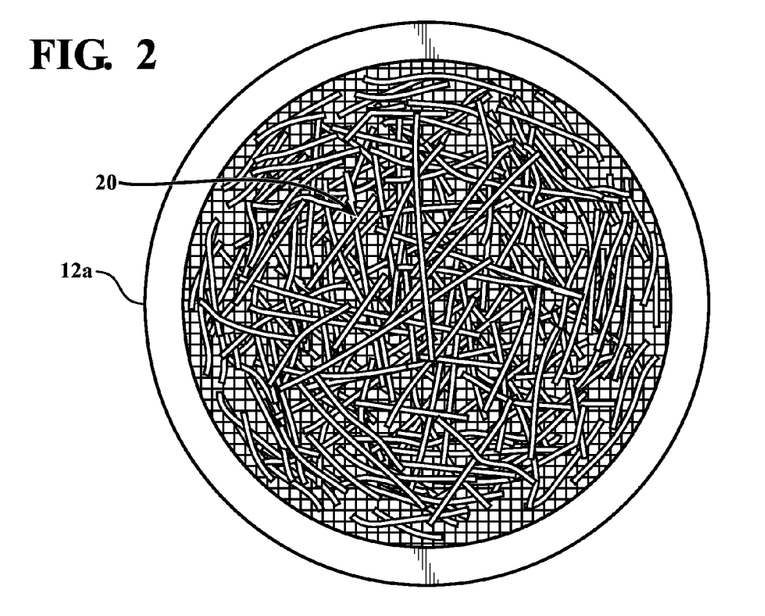
FIG. 2 is a top view of the top sieve of the prior art sieve stack of FIG. 1 showing a bundle of adhered fibers.

FIG. 2 is a top view of the top sieve 12a of the prior art sieve stack 10 of FIG. 1 showing an adhered-fiber bundle 20. Despite the use of a non-polar liquid or additive, many of the fibers in a sample can cling to one another and remain present in a bundle 20 in the top sieve 12a after the mixture has been passed through each of the sieves 12a-e in the sieve stack 10. Physically stifling the fibers to separate them from the bundle 20 can break the fibers, leading to an inaccurate length distribution. Allowing the fibers to remain in the bundle 20 can also lead to an inaccurate length distribution, as the smaller fibers fail to pass through the top sieve 12a and add weight to the top sieve 12a that should be present at other sieves 12b-e in the sieve stack 10. Determining an accurate weight distribution for the fibers from the sample requires an improvement to the sieve-based system described above.

Figure 3:
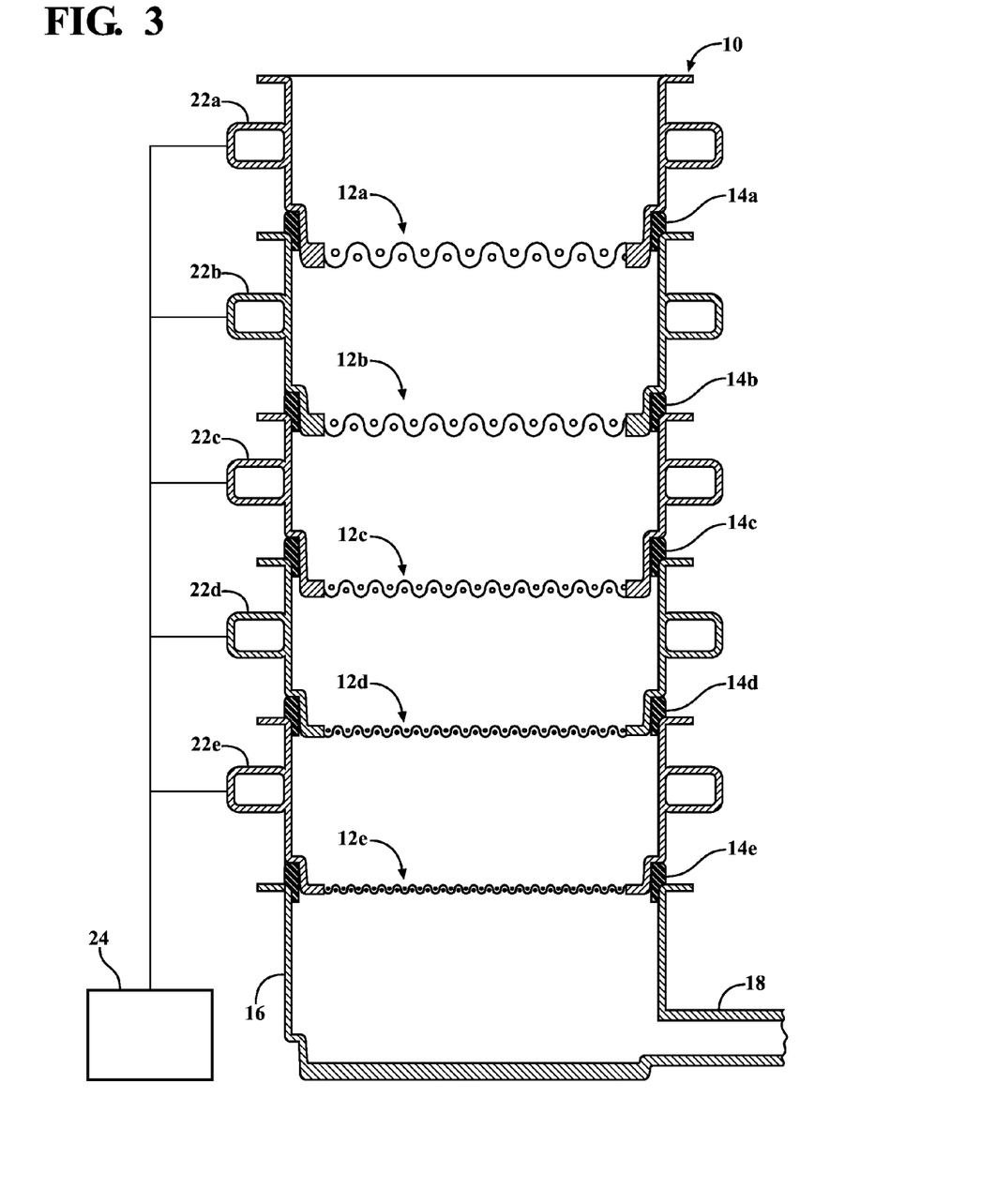
FIG. 3 is a is a sectional side view of an improved apparatus for sorting fibers including the sieve stack of FIG. 1.

FIG. 3 is a sectional side view of an improved apparatus for sorting fibers including the sieve stack 10 of FIG. 1. The improved apparatus includes the sieves 12a-e, seals 14a-e, collection unit 16, and drain 18 as shown in FIG. 1. The improvement can be tied to the use of one or more sonicating devices 22a-e to progressively apply one or more frequencies of sound energy to each of the sieves 12a-e according to commands received from a control device 24. Sonication is generally known. In one implementation of sonication, an ultrasonic electric generator transforms alternating current power to high frequency electrical energy to drive a piezoelectric converter. The frequencies produced can be ultrasonic frequencies. The converter then transforms electrical energy to mechanical vibration for amplification and transmission. The vibration can travel along the length of a probe configured for immersion into a liquid, or along another surface, such as a plate, for attachment to an existing structure.

The sectional view shown in FIG. 3 indicates that this example set of sonicating devices 22a-e has a ring-style structure with each sonicating device 22a-e attached or coupled to surround the vertical walls of each sieve 12a-e. The sonicating devices 22a-e could also be configured for communication directly with the mixture disposed within each sieve 12a-e. For example, the sonicating devices 22a-e could include probe-style tips for insertion through the walls of each sieve 12a-e (not shown). The control device 24 is in communication with each sonicating device 22a-e and is configured to allow an operator of the sieve stack 10 to apply frequencies of sound energy of specified order, magnitude, and duration to each sieve 12a-e. That is, the operator can use the control device 24 to implement a pattern of frequencies.

For example, the application of two or more frequencies can be progressive through each of the sieves 12a-e in the sieve stack 10. In one example of progressive frequency application, the first frequency can be applied to the first sieve 12a for a predetermined duration, stopped, and then subsequently applied to each progressive level of the sieve stack 10: sieve 12b, then sieve 12c, then sieve 12d, up to the last sieve 12e. The first frequency can be tuned to excite the shortest fiber length. By progressively applying the first frequency to each progressive level of the sieve stack 10, the shortest fibers are being passed one level at a time from the top of the sieve stack 10 to the bottom of the sieve stack 10. Next, a second frequency can be applied to the first sieve 12a for a predetermined duration, stopped, and then subsequently applied to each progressive level of the sieve stack 10. The second frequency can be tuned to excite the second shortest fiber length. This progressive application can continue for more distinct frequencies, as many as are needed to distribute all of the fiber lengths.

In the example shown in FIG. 3, five frequencies tuned to five fiber lengths would correlate to a sieve stack 10 having five sieves 12a-e, as each frequency can excite fibers of a different length. In this example, the first frequency can be higher than the second frequency, which can be higher than the third frequency, etc. That is, the highest frequency can be used to excite the fibers of the shortest length, the next highest frequency can be used to excite the fibers of the next shortest length, etc. In another example, the fibers can be passed by applying progressively decreasing frequencies from the highest frequency to the lowest frequency to the first sieve 12a in the sieve stack 10 and subsequently to each progressive layer up to the last or bottom sieve 12e in the sieve stack 10. In the example shown in FIG. 3, five distinct frequencies would be applied from the highest to the lowest to the first sieve 12a before applying the same five distinct frequencies in the same order to the second sieve 12b, etc. Each set of passable lengths of fiber would thus be excited to move from the first sieve 12a to the second sieve 12b before moving the next set of passable lengths of fiber from the second sieve 12b to the third sieve 12c.

Since each sieve 12a-e is configured to collect a progressively shorter fiber from the mixture when measured from bottom to top, the progressive application of frequencies will sort the fibers by length, longest in the top sieve 12a and shortest in the bottom sieve 12e. After a complete set of frequencies has been applied at each level of the sieve stack 10, the liquid from the mixture can be drained from the sieve stack 10, using drain 18. The fibers remaining in each level of the sieve stack 10 can then be quantified to determine the length distribution.

Figure 4A:
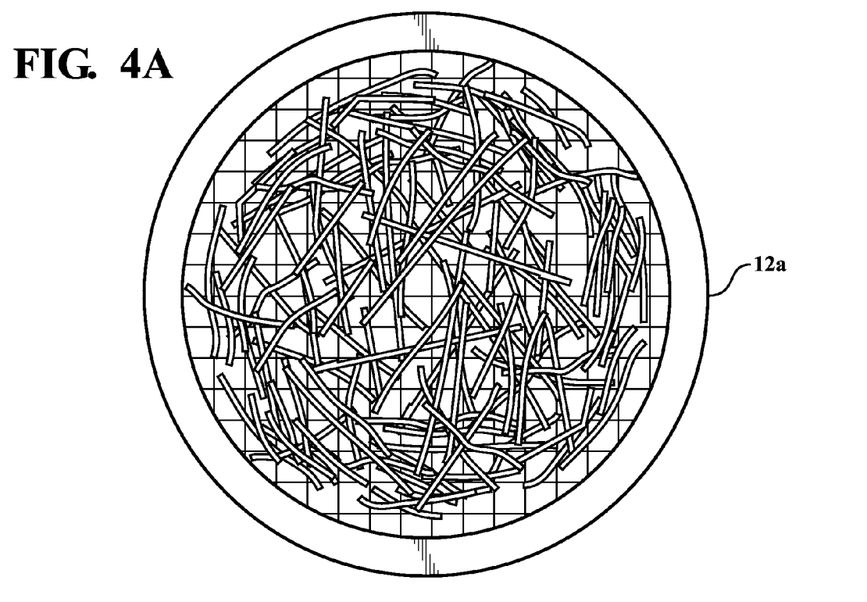
FIGS. 4A-E are top comparison views of each sieve in the sieve stack after use of the improved apparatus for sorting fibers of FIG. 3.
Figure 4B:
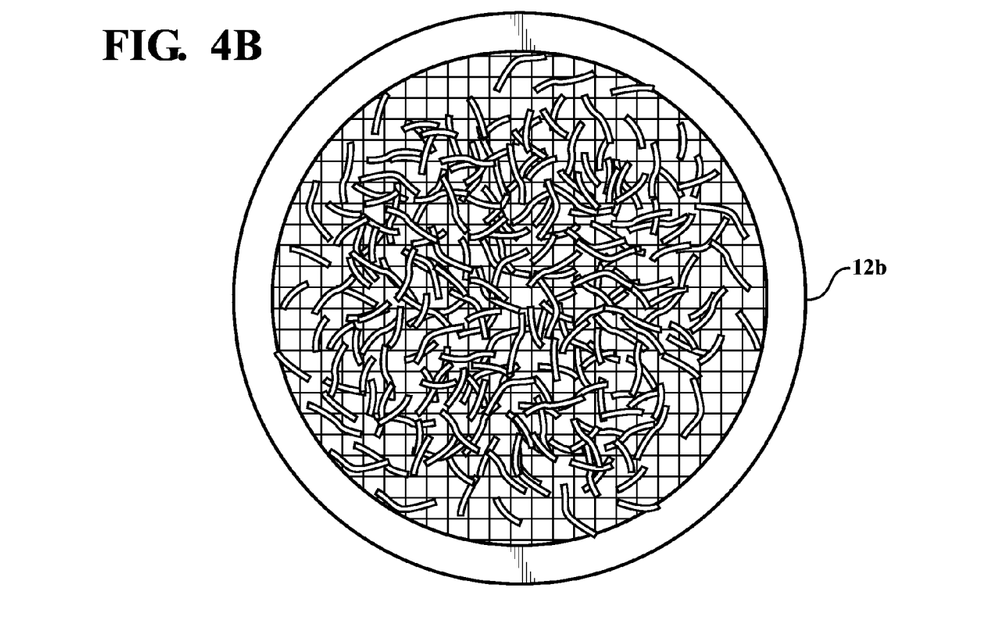
Figure 4C:
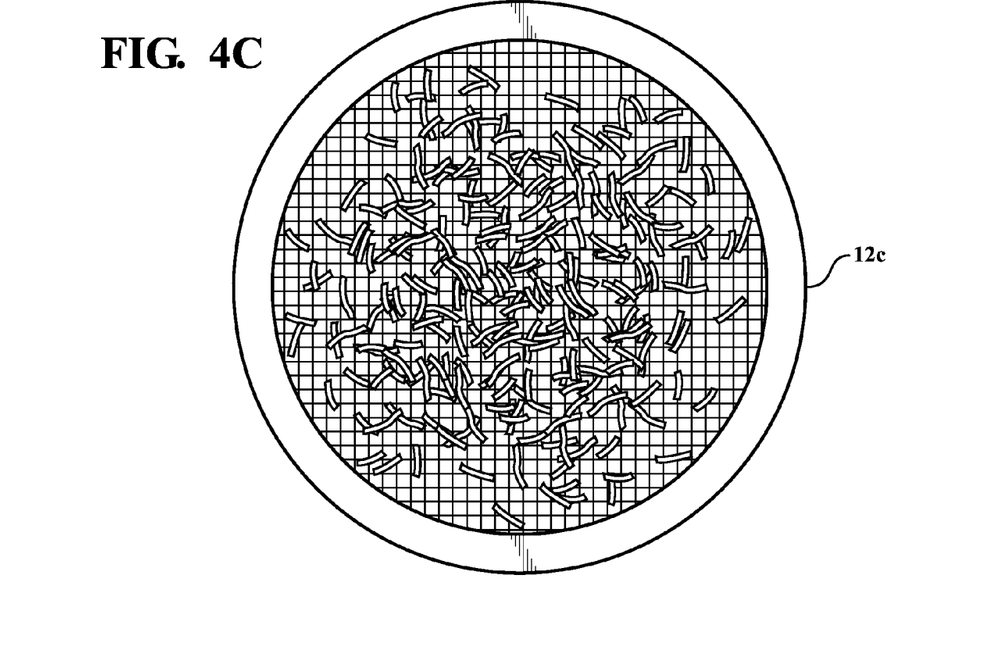
Figure 4D:
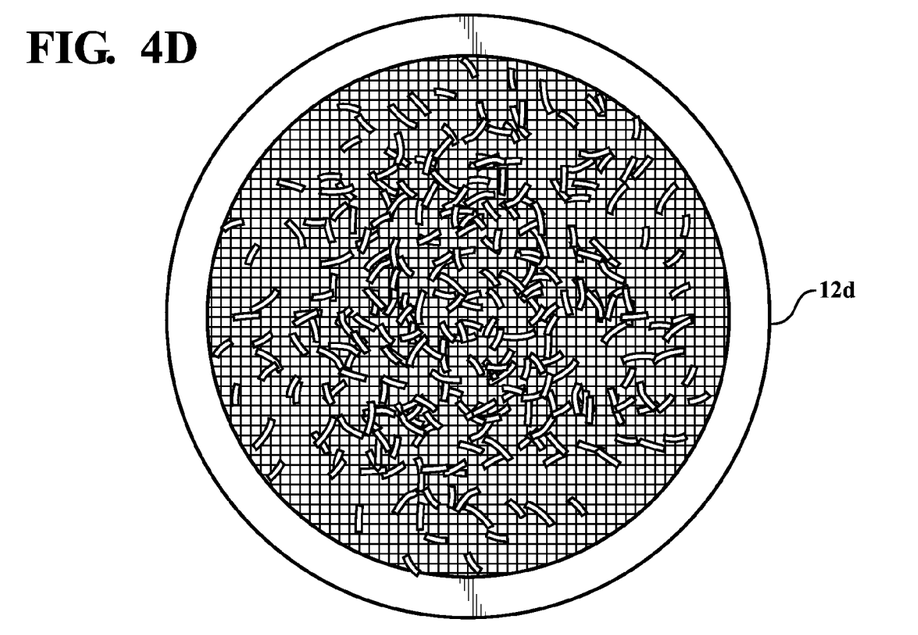
Figure 4E:
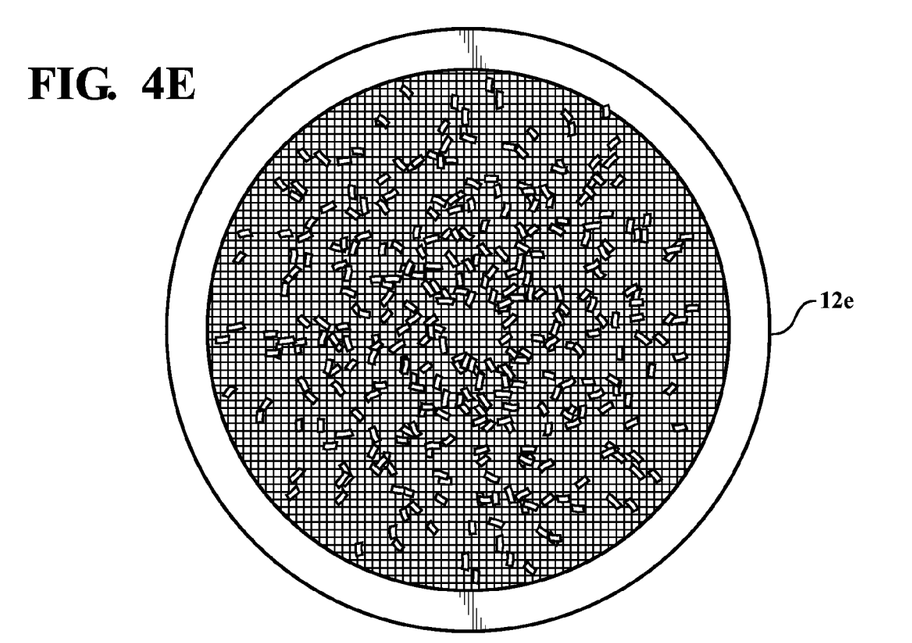

FIGS. 4A-E are a top comparison views of each sieve 12a-e in the sieve stack 10 after use of the improved apparatus for sorting fibers of FIG. 3. In the example shown here, the longest fibers, for example greater than 10 mm in length, are collected in sieve 12a as shown in FIG. 4A and the shortest fibers, for example, in the range of 0.25 mm-1 mm are collected in sieve 12e as shown in FIG. 4E with fibers of intermediate length collected by the intermediate sieves 12b-d as shown in FIGS. 4B-D. Once separated, each sieve 12a-e can be dried and weighed. The difference in weight of each sieve 12a-e before and after the mixture was passed through the sieve stack 10 indicates the fiber length distribution within the sample FRP, and thus the whole FRP. The FRP can be sampled in more than one location, or additional FRPs of the same design or source can be sampled. The additional samples can also be processed to determine fiber length distribution for validation purposes.

Figure 5:
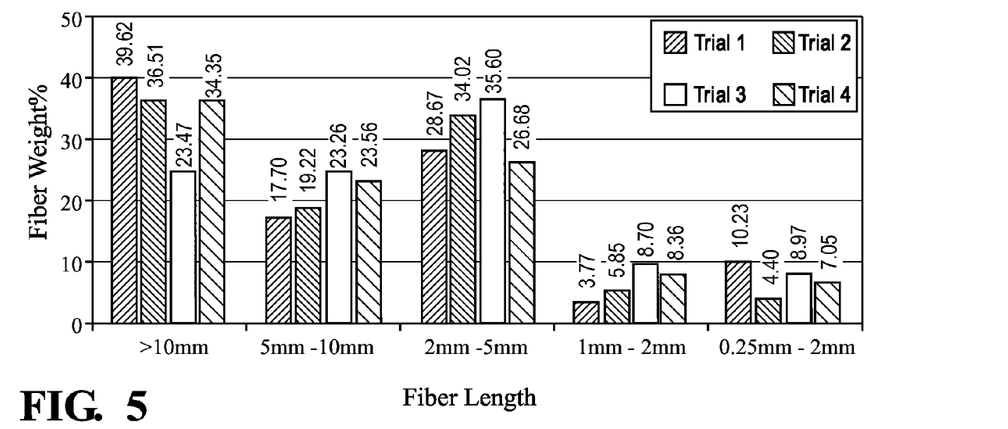
FIG. 5 is chart showing example weight distributions of fibers by sieve size.

FIG. 5 is chart showing example weight distributions of fibers by sieve size. In this example, there were five sieves such as sieves 12a-e, with each sieve 12a-e configured to collect a different range of fiber lengths. For example, sieve 12a can be configured to collect fibers greater than 10 mm in length and sieve 12e can be configured to collect fibers between 0.25 mm and 1 mm in length. Any particulates in the mixture smaller than 0.25 mm would pass through all of the sieves 12a-e and be removed with the liquid from the drain 18. The chart shows four trials, each represented by a different bar pattern. The height of the bars indicates the percentage of weight for that length of fiber as part of the total weight. As shown here, most of the weight for the sample trials shown was in fibers greater than 10 mm in length, followed by fibers between 2 mm and 5 mm in length, followed by fibers between 5 mm and 10 mm in length, followed by fibers between 0.25 mm and 1 mm in length, and finally, followed by fibers between 1 mm and 2 mm in length.

Figure 6:
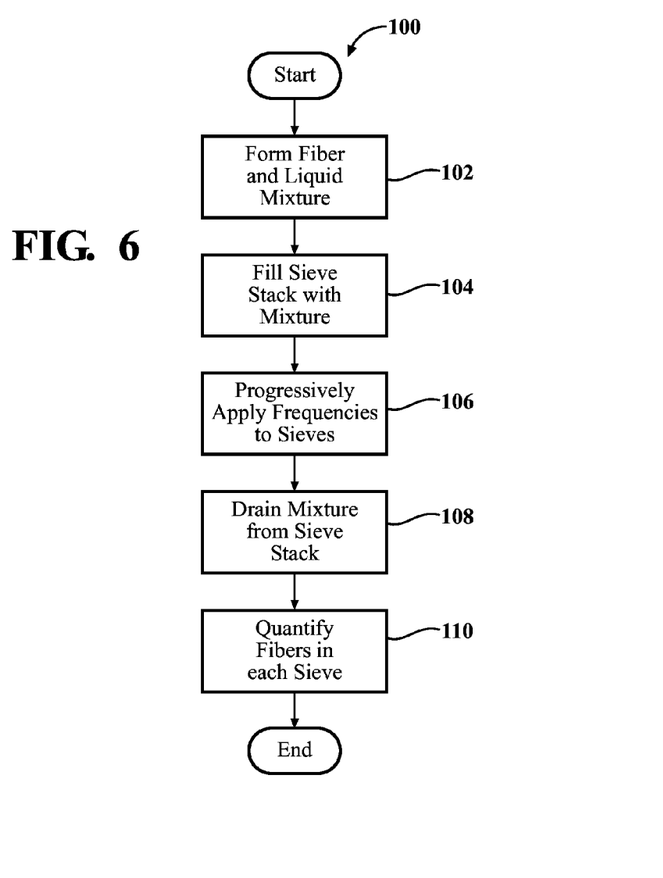
FIG. 6 is a flow chart of a process for sorting and determining the length distribution of fibers using the improved apparatus of FIG. 3.

FIG. 6 is a flow chart of a process 100 for sorting and determining the length distribution of fibers using the improved apparatus of FIG. 3. In step 102, the fibers isolated from the FRP can be immersed in a liquid, for example, a non-polar liquid or fluid treated with a non-polar additive, to form a mixture. In step 104, the mixture can be placed in a sieve stack 10, for example, the sieve stack 10 can be filled with the mixture by pouring the mixture into the sieve stack 10. Each sieve 12a-e in the sieve stack 10 can be configured to collect a progressively shorter fiber from the mixture as measured from bottom to top of the sieve stack 10 and seals 14a-e can be present between the sieves 12a-e to prevent the mixture from leaking from the sieve stack 10.

In step 106, a predetermined number of frequencies of sound energy can be applied progressively to the sieves 12a-e in the sieve stack 10. The frequencies can be ultrasonic frequencies. As described above, the number of frequencies to apply can be based on the number of sieves 12a-e in the sieve stack 10. The number of sieves 12a-e can be chosen based on the number or range of lengths of fibers present in the mixture. The higher the number of sieves, the more distinction that can be made in the overall length distribution of the fibers, which can be useful for quality control purposes. The progressive application of frequencies can include applying one frequency at each level in the sieve stack 10 before applying a next frequency to each level in the sieve stack 10 as well as applying the full range of frequencies to one level of the sieve stack 10 before applying the full range of frequencies to the next level in the sieve stack 10, among other patterns. The pattern, that is the magnitude, duration, and order of frequencies to be applied, is chosen by the operator and implemented using the control device 24.

In step 108, the mixture is drained from the sieve stack 10. Only the fibers smaller than the finest grained sieve 12e will be removed with the liquid. The rest of the fibers will remain on the sieves 12a-e, with each sieve 12a-e designed to collect a progressively shorter fiber from the mixture. In step 110, the fibers in each sieve 12a-e in the sieve stack 10 are quantified. As explained above, the sieves 12a-e can be dried and weighed both before and after the mixture passes through the sieves 12a-e such that the weight comparison can be used to determine the overall fiber length distribution by percentage in the sample. An example fiber length distribution was shown in FIG. 5.

The foregoing description relates to what are presently considered to be the most practical embodiments. It is to be understood, however, that the disclosure is not to be limited to these embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A method of sorting and determining the length distribution of fibers, comprising:
    immersing the fibers in a liquid to form a mixture;
    filling a stack of sieves with the mixture;
    progressively applying two or more ultrasonic frequencies of sound energy to each sieve in the stack of sieves;
    draining the mixture from the stack of sieves; and
    quantifying the collected fibers in each sieve in the stack of sieves.

2. The method of claim 1, wherein the liquid is one of a polar liquid, a non-polar liquid, and a polar liquid treated with an additive.

3. The method of claim 1, wherein each frequency in the two or more ultrasonic frequencies excites fibers of a different length.

4. The method of claim 1, wherein progressively applying two or more ultrasonic frequencies of sound energy includes:
    applying a first frequency to the first sieve in the stack of sieves and subsequently to each progressive sieve up to the last sieve in the stack of sieves; and
    after the first frequency has been applied to each progressive sieve in the stack of sieves, applying a second frequency to the first sieve in the stack of sieves and subsequently to each progressive sieve up to the last sieve in the stack of sieves.

5. The method of claim 4, wherein the first frequency is higher than the second frequency.

6. The method of claim 1, wherein progressively applying two or more ultrasonic frequencies of sound energy includes:
    applying progressively decreasing frequencies from a highest frequency to a lowest frequency to the first sieve in the stack of sieves and subsequently to each progressive sieve up to the last sieve in the stack of sieves.

7. The method of claim 1, wherein each sieve in the stack of sieves is configured to collect a progressively shorter fiber from the mixture.

8. The method of claim 1, wherein the quantifying includes weighing the collected fibers in each sieve in the stack.

9. A method of sorting and determining the length distribution of fibers, comprising:
    immersing the fibers in a liquid to form a mixture;
    placing the mixture into a stack of sieves;
    progressively applying a predetermined number of ultrasonic frequencies of sound energy to each sieve in the stack of sieves;
    draining the mixture from the stack of sieves; and
    quantifying the collected fibers in each sieve in the stack of sieves.

10. The method of claim 9 wherein each of the ultrasonic frequencies of sound energy excites fibers of different lengths.

11. The method of claim 9 wherein the predetermined number of ultrasonic frequencies is based on the number of sieves in the stack of sieves.

12. The method of claim 9 wherein progressively applying includes applying each of the predetermined number of ultrasonic frequencies first to the top sieve and then to each progressively lower sieve up to and including the last sieve in the stack of sieves.

13. The method of claim 9 wherein each sieve in the stack of sieves is configured to collect a progressively shorter fiber from the mixture.

14. The method of claim 9, wherein the liquid is one of a polar liquid, a non-polar liquid, and a polar liquid treated with an additive.

15. The method of claim 9, wherein the quantifying includes weighing the collected fibers in each sieve in the stack.

* * * * *